US008906225B2

(12) United States Patent
Lewis et al.

(10) Patent No.: US 8,906,225 B2
(45) Date of Patent: Dec. 9, 2014

(54) METALLOPHOSPHATE MOLECULAR SIEVES, METHODS OF PREPARATION AND USE

(75) Inventors: Gregory J. Lewis, Santa Cruz, CA (US); Lisa M. Knight, Chicago, IL (US); Paulina Jakubczak, Elk Grove Village, IL (US); Justin E. Stanczyk, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 404 days.

(21) Appl. No.: 13/537,337

(22) Filed: Jun. 29, 2012

(65) Prior Publication Data

US 2014/0004024 A1    Jan. 2, 2014

(51) Int. Cl.
*C10G 47/04* (2006.01)
*B01D 15/08* (2006.01)
*B01D 53/22* (2006.01)

(52) U.S. Cl.
USPC ............. 208/108; 208/46; 208/109; 208/114; 585/466; 585/640; 585/721; 95/45; 210/634; 210/660

(58) Field of Classification Search
USPC ......... 95/45; 210/634, 660; 208/46, 108, 109, 208/114; 585/466, 640, 721
See application file for complete search history.

(56) References Cited

U.S. PATENT DOCUMENTS

| | | | |
|---|---|---|---|
| 4,310,440 A | | 1/1982 | Wilson et al. |
| 4,440,871 A | | 4/1984 | Lok et al. |
| 4,567,029 A | | 1/1986 | Wilson et al. |
| 4,744,970 A | * | 5/1988 | Lok et al. ...................... 423/306 |
| 4,870,222 A | | 9/1989 | Bakas et al. |
| 4,973,785 A | | 11/1990 | Lok et al. |
| 5,126,308 A | | 6/1992 | Barger et al. |
| 5,157,196 A | | 10/1992 | Crossland et al. |
| 5,157,197 A | | 10/1992 | Cooper et al. |
| 6,776,975 B2 | | 8/2004 | Wilson et al. |

OTHER PUBLICATIONS

AFV Framework from Database of Zeolite Structures, available online at www.iza-structure.org/databases accessed Sep. 23, 2014.*
Smith et al, "Enumeration of 4-connected 3-dimensional nets and classification of framework silicates: the infinite set of ABC-6 nets; the Archimedean and σ-related nets", American Mineralogist, 1981, vol. 66, pp. 777-788.
Gatter, "Stability of Framework Aluminum in the New Zeolite UZM-5", Studies in Surface Science and Catalysis, 2004, vol. 154, pp. 1324-1331.

* cited by examiner

*Primary Examiner* — In Suk Bullock
*Assistant Examiner* — Bradley Etherton
(74) *Attorney, Agent, or Firm* — Maryann Maas

(57) ABSTRACT

A new family of crystalline microporous metallophosphates designated AlPO-57 has been synthesized. These metallophosphates are represented by the empirical formula $$R^+_r M_m^{n+} EP_x Si_y O_z$$

where R is an organoammonium cation such as the DEDMA$^+$, M is a divalent framework metal such as an alkaline earth or transition metal, and E is a framework element such as aluminum or gallium. The microporous AlPO-57 compositions are characterized by a new unique ABC-6 net structure and have catalytic properties for carrying out various hydrocarbon conversion processes and separation properties for separating at least one component.

20 Claims, No Drawings

METALLOPHOSPHATE MOLECULAR SIEVES, METHODS OF PREPARATION AND USE

FIELD OF THE INVENTION

This invention relates to a new family of charged microporous metallophosphate molecular sieves designated AlPO-57. They are represented by the empirical formula of:

$$R^+_r M_m^{n+} EP_x Si_y O_z$$

where M is a divalent framework metal such as magnesium or zinc, R is an organoammonium cation such as diethyldimethylammonium and E is a trivalent framework element such as aluminum or gallium.

BACKGROUND OF THE INVENTION

Zeolites are crystalline aluminosilicate compositions which are microporous and which are formed from corner sharing $AlO_2^-$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on the outside surfaces of the zeolite as well as on internal surfaces within the pores of the zeolite.

It is possible to use essentially the same techniques to produce microporous materials of other compositions, e.g., non-zeolitic compositions. In 1982, Wilson et. al. first reported aluminophosphate molecular sieves, the so-called AlPOs, which are microporous materials that have many of these same properties of zeolites, although they are silica free, composed of $AlO_2^-$ and $PO_2^+$ tetrahedra (See U.S. Pat. No. 4,310,440). Subsequently, charge was introduced to the neutral aluminophosphate frameworks via the substitution of $SiO_2$ tetrahedra for $PO_2^+$ tetrahedra to produce the SAPO molecular sieves (See U.S. Pat. No. 4,440,871). Another way to introduce framework charge to neutral aluminophosphates is to substitute $[M^{2+}O_2]^{2-}$ tetrahedra for $AlO_2^-$ tetrahedra, which yield the MeAPO molecular sieves (see U.S. Pat. No. 4,567,029). It is furthermore possible to introduce framework charge on AlPO-based molecular sieves via the simultaneous introduction of $SiO_2$ and $[M^{2+}O_2]^{2-}$ tetrahedra to the framework, giving MeAPSO molecular sieves (See U.S. Pat. No. 4,973,785).

Applicants have synthesized a new family of charged microporous metallophosphate framework materials with SAPO, MeAPO, and MeAPSO compositions designated AlPO-57. The AlPO-57 materials have a unique topology that falls in the class of structures known as ABC-6 nets (See American Mineralogist, 66, 777-788 (1981)). The microporous AlPO-57 materials can be prepared with the diethyldimethylammonium ($DEDMA^+$) or methyltriethylammonium ($MTEA^+$) structure directing agents.

SUMMARY OF THE INVENTION

As stated, the present invention relates to a new family of microporous metallophosphate molecular sieves designated AlPO-57. Accordingly, one embodiment of the invention is a microporous crystalline material having a three-dimensional framework of at least $EO_2^-$ and $PO_2^+$ tetrahedral units and furthermore, at least one of $[M^{2+}O_2]^{2-}$ and $SiO_2$ tetrahedral units and an empirical composition in the as synthesized and anhydrous basis expressed by an empirical formula of:

$$R^+_r M_m^{2+} EP_x Si_y O_z$$

where M is at least one framework divalent metal cation selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, R is an organoammonium cation selected from the group consisting of ethyltrimethylammonium ($ETMA^+$), diethyldimethylammonium ($DEDMA^+$), methyltriethylammonium ($MTEA^+$), tetraethylammonium ($TEA^+$), tetrapropylammonium ($TPA^+$) and mixtures thereof, "r" is the mole ratio of R to E and has a value of about 0.1 to about 2.0, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, "m"+"y"≥0.10, and "z" is the mole ratio of O to E and has a value determined by the equation:

$$z = (2 \cdot m + r + 3 + 5 \cdot x + 4 \cdot y)/2$$

and is characterized in that it has the x-ray diffraction pattern having at least the d-spacings and intensities set forth in Table A:

TABLE A

| 2Θ | d (Å) | I/I₀ % |
|---|---|---|
| 7.85-7.36 | 11.25-12.00 | w |
| 10.49-10.11 | 8.43-8.74 | m-vs |
| 13.40-13.03 | 6.60-6.79 | w-m |
| 15.40-15.13 | 5.75-5.85 | w |
| 17.00-16.56 | 5.21-5.35 | m-s |
| 19.41-18.87 | 4.57-4.70 | w-m |
| 20.49-20.03 | 4.33-4.43 | w |
| 21.09-20.35 | 4.21-4.36 | w-m |
| 21.66-21.24 | 4.10-4.18 | m-vs |
| 22.43-21.98 | 3.96-4.04 | m-vs |
| 23.14-22.78 | 3.84-3.90 | w-m |
| 26.11-25.58 | 3.41-3.48 | w |
| 26.91-26.35 | 3.31-3.38 | w-m |
| 29.16-28.68 | 3.06-3.11 | m-s |
| 31.94-31.36 | 2.80-2.85 | m |
| 35.02-34.33 | 2.56-2.61 | w-m |
| 35.74-35.16 | 2.51-2.55 | w |
| 42.61-41.99 | 2.12-2.15 | w |
| 48.93-48.10 | 1.86-1.89 | w |
| 49.50-48.65 | 1.84-1.87 | w |
| 50.98-50.37 | 1.79-1.81 | w |
| 54.94-54.23 | 1.67-1.69 | w |

Another embodiment of the invention is a process for preparing the crystalline microporous metallophosphate molecular sieve described above. The process comprises forming a reaction mixture containing reactive sources of R, E, P, and either one or both of M and Si and heating the reaction mixture at a temperature of about 60° C. to about 200° C. for a time sufficient to form the molecular sieve, the reaction mixture having a composition expressed in terms of mole ratios of the oxides of:

$aR_2O:bMO:E_2O_3:cP_2O_5:dSiO_2:eH_2O$ where "a" has a value of about 0.75 to about 16, "b" has a value of about 0 to about 2, "c" has a value of about 0.8 to about 8, "d" has a value of about 0 to about 4, and "e" has a value from 30 to 800.

Yet another embodiment of the invention is a hydrocarbon conversion process using the above-described molecular sieve as a catalyst. The process comprises contacting at least one hydrocarbon with the molecular sieve at conversion conditions to generate at least one converted hydrocarbon.

Still another embodiment of the invention is a separation process using the crystalline AlPO-57 material. The process may involve separating mixtures of molecular species or removing contaminants by contacting a fluid with the AlPO-57 molecular sieve. Separation of molecular species can be based either on the molecular size (kinetic diameter) or on the degree of polarity of the molecular species. Removing contaminants may be by ion exchange with the molecular sieve.

DETAILED DESCRIPTION OF THE INVENTION

Applicants have prepared a family of microporous metallophosphate materials whose topological structure is unique. In their paper "Enumeration of 4-connected 3-dimensional nets and classification of framework silicates: the infinite set of ABC-6 nets; the Archimedean and σ-related nets," Smith and Pluth state "To a first approximation, all silicates belonging to the ABC-6net family have x-ray diffraction patterns which can be indexed on a hexagonal prismatic unit cell with lattice parameters a~13.0±0.3 Å and c~p×(2.6±0.1 Å)." (See American Mineralogist, 66, 777-788 (1981)). One particular DEDMA-Zn—Al—P—O composition of AlPO-57 indexes on a hexagonal unit cell with lattice parameters a=13.282 Å and c=12.508 Å, which suggests an ABC-6 net structure with the stacking sequence repeating every 5 layers along the c-axis (p=12.5/2.5=5). This is the first known example of an ABC-6 net structure with a 5-layer repeats, hence the topology of the AlPO-57 family of materials is unique. The instant microporous crystalline material (AlPO-57) has an empirical composition in the as-synthesized form and on an anhydrous basis expressed by the empirical formula:

$R^+_r M^{2+}_m EP_x Si_y O_z$ where M is at least one divalent framework metal cation and is selected from the group consisting of alkaline earth and transition metals. Specific examples of the M cations include but are not limited to beryllium, magnesium, cobalt(II), manganese, zinc, iron(II), nickel and mixtures thereof. R is an organoammonium cation, examples of which include but are not limited to the choline cation, $[(CH_3)_3N(CH_2)_2OH]^+$, tetramethylammonium cation (TMA$^+$), ethyltrimethylammonium (ETMA$^+$), trimethylpropylammonium, diethyldimethylammonium (DEDMA$^+$), methyltriethylammonium (MTEA$^+$), trimethylpropylammonium, dimethyldiethanolammonium, tetraethylammonium (TEA$^+$), tetrapropylammonium (TPA$^+$) and mixtures thereof and "r" is the mole ratio of R to E and varies from about 0.1 to about 2.0. The value of "m" is the mole ratio of M to E and varies from 0 to about 1.0, "x" is mole ratio of P to E and varies from 0.5 to about 2.0. The ratio of silicon to E is represented by "y" which varies from about 0 to about 1.0 and "m"+"y"≥0.1. E is a trivalent element which is tetrahedrally coordinated, is present in the framework and is selected from the group consisting of aluminum, gallium, iron(III) and boron. Lastly, "z" is the mole ratio of O to E and is given by the equation:

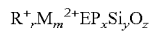
$z=(2·m+r+3+5x+4·y)/2$.

The microporous crystalline metallophosphate material, AlPO-57, is prepared by a hydrothermal crystallization of a reaction mixture prepared by combining reactive sources of R, E, phosphorous, and one or both of M and silicon. When E is aluminum, the sources of include but are not limited to aluminum alkoxides, precipitated aluminas, aluminum metal, aluminum hydroxide, aluminum salts and alumina sols. Specific examples of aluminum alkoxides include, but are not limited to aluminum ortho sec-butoxide and aluminum ortho isopropoxide. Sources of other E elements include but are not limited to organoammonium borates, boric acid, precipitated gallium oxyhydroxide, gallium sulfate, ferric sulfate, and ferric chloride. Sources of phosphorus include, but are not limited to, orthophosphoric acid, phosphorus pentoxide, and ammonium dihydrogen phosphate. Sources of silica include but are not limited to tetraethylorthosilicate, colloidal silica, and precipitated silica. Sources of the M metals include the halide salts, nitrate salts, acetate salts, and sulfate salts of the respective alkaline earth and transition metals. R is an organoammonium cation selected from the group consisting of choline, TMA$^+$, ETMA$^+$, DEDMA$^+$, MTEA$^+$, TPA$^+$, trimethylpropylammonium, dimethyldiethanolammonium and mixtures thereof, and the sources include the hydroxide, chloride, bromide, iodide and fluoride compounds. Specific examples include without limitation choline hydroxide and choline chloride, ethyltrimethylammonium hydroxide, diethyldimethylammonium hydroxide, diethyldimethylammonium chloride, methyltriethylammonium hydroxide, and methyltriethylammonium chloride. In a specific embodiment, R is at least DEDMA$^+$. In another embodiment, R is at least MTEA$^+$. In another embodiment, R is a combination of DEDMA$^+$ and at least one organoammonium cation selected from the group consisting of choline, TMA$^+$, ETMA$^+$, MTEA$^+$, trimethylpropylammonium, dimethyldiethanolammonium, TEA$^+$, and TPA$^+$. In yet another embodiment, R is a combination of MTEA$^+$ and at least one organoammonium cation selected from the group consisting of choline, TMA$^+$, ETMA$^+$, DEDMA$^+$, trimethylpropylammonium, dimethyldiethanolammonium, TEA$^+$, and TPA$^+$.

The reaction mixture containing reactive sources of the desired components can be described in terms of molar ratios of the oxides by the formula:

$aR_2O:bMO:E_2O_3:cP_2O_5:dSiO_2:eH_2O$ where "a" varies from about 0.75 to about 16, "b" varies from about 0 to about 2, "c" varies from about 0.8 to about 8, "d" varies from about 0 to about 2, and "e" varies from 30 to 800. If alkoxides are used, it is preferred to include a distillation or evaporative step to remove the alcohol hydrolysis products. The reaction mixture is now reacted at a temperature of about 60° C. to about 200° C. and preferably from about 125° C. to about 200° C. for a period of about 1 day to about 3 weeks and preferably for a time of about 2 days to about 10 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. AlPO-57 seeds can optionally be added to the reaction mixture in order to accelerate the formation of the desired microporous composition.

The AlPO-57 aluminophosphate-based material, which is obtained from the above-described process, is characterized by the x-ray diffraction pattern, having at least the d-spacings and relative intensities set forth in Table A below.

TABLE A

| 2Θ | d (Å) | I/I₀ % |
|---|---|---|
| 7.85-7.36 | 11.25-12.00 | w |
| 10.49-10.11 | 8.43-8.74 | m-vs |
| 13.4-13.03 | 6.60-6.79 | w-m |
| 15.4-15.13 | 5.75-5.85 | w |
| 17-16.56 | 5.21-5.35 | m-s |
| 19.41-18.87 | 4.57-4.70 | w-m |
| 20.49-20.03 | 4.33-4.43 | w |
| 21.09-20.35 | 4.21-4.36 | w-m |
| 21.66-21.24 | 4.10-4.18 | m-vs |
| 22.43-21.98 | 3.96-4.04 | m-vs |
| 23.14-22.78 | 3.84-3.90 | w-m |
| 26.11-25.58 | 3.41-3.48 | w |
| 26.91-26.35 | 3.31-3.38 | w-m |
| 29.16-28.68 | 3.06-3.11 | m-s |
| 31.94-31.36 | 2.80-2.85 | m |
| 35.02-34.33 | 2.56-2.61 | w-m |
| 35.74-35.16 | 2.51-2.55 | w |
| 42.61-41.99 | 2.12-2.15 | w |
| 48.93-48.10 | 1.86-1.89 | w |
| 49.50-48.65 | 1.84-1.87 | w |
| 50.98-50.37 | 1.79-1.81 | w |
| 54.94-54.23 | 1.67-1.69 | w |

The AlPO-57 may be modified in many ways to tailor it for use in a particular application. Modifications include calcination, ammonia calcinations, ion-exchange, steaming, various acid extractions, ammonium hexafluorosilicate treatment, or any combination thereof, as outlined for the case of UZM-4 in U.S. Pat. No. 6,776,975 B1 which is incorporated by reference in its entirety. Properties that are modified include porosity, adsorption, framework composition, acidity, thermal stability, etc.

As synthesized, the AlPO-57 material will contain some of the exchangeable or charge balancing cations in its pores. These exchangeable cations can be exchanged for other cations, or in the case of organic cations, they can be removed by heating under controlled conditions. A preferred method of removing organic cations from the pores is ammonia calcination. Calcination in air converts organic cations in the pores to protons, which can, for example, lead to some removal of Al from the framework upon exposure to water vapor. When the calcination is carried out in an ammonia atmosphere, the organic cation in the pore is replaced by $NH_4^+$ cation and the framework remains intact (See Studies in Surface Science, (2004) vol. 154, p. 1324-1331). Typical conditions for ammonia calcinations include the use of gaseous anhydrous ammonia flowing at a rate of 1.1 l/min while ramping the sample at 5° C./min to 500° C. and holding at that temperature for a time ranging from 5 minutes to an hour. The resulting ammonium form of AlPO-57 has essentially the diffraction pattern of Table A. The ammonium form of AlPO-57 may then be ion-exchanged to any other form, resulting in a material with a modified composition, AlPO-57M, given by the empirical formula:

$$M'^{p+}_n M^{2+}_m EP_x Si_y O_z$$

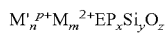

where M is at least one divalent metal cation selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, M' is $NH_4^+$, $H^+$, alkali metals, alkaline earth metals, transition metals and rare earth metals and mixtures thereof, "n" is the mole ratio of M' to E and has a value of about 0.03 to about 2.0, "p" is the weighted average valence of M', E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, "m"+"y"≥0.1, and "z" is the mole ratio of O to E and has a value determined by the equation:

$$z = (p \cdot n + 2 \cdot m + 3 + 5 \cdot x + 4 \cdot y)/2$$

and is characterized in that it has the x-ray diffraction pattern having at least the d-spacings and intensities set forth in Table A:

TABLE A

| 2Θ | d (Å) | I/I₀ % |
|---|---|---|
| 7.85-7.36 | 11.25-12.00 | w |
| 10.49-10.11 | 8.43-8.74 | m-vs |
| 13.40-13.03 | 6.60-6.79 | w-m |
| 15.40-15.13 | 5.75-5.85 | w |
| 17.00-16.56 | 5.21-5.35 | m-s |
| 19.41-18.87 | 4.57-4.70 | w-m |
| 20.49-20.03 | 4.33-4.43 | w |
| 21.09-20.35 | 4.21-4.36 | w-m |
| 21.66-21.24 | 4.10-4.18 | m-vs |
| 22.43-21.98 | 3.96-4.04 | m-vs |
| 23.14-22.78 | 3.84-3.90 | w-m |
| 26.11-25.58 | 3.41-3.48 | w |
| 26.91-26.35 | 3.31-3.38 | w-m |
| 29.16-28.68 | 3.06-3.11 | m-s |
| 31.94-31.36 | 2.80-2.85 | m |
| 35.02-34.33 | 2.56-2.61 | w-m |
| 35.74-35.16 | 2.51-2.55 | w |
| 42.61-41.99 | 2.12-2.15 | w |
| 48.93-48.10 | 1.86-1.89 | w |
| 49.50-48.65 | 1.84-1.87 | w |
| 50.98-50.37 | 1.79-1.81 | w |
| 54.94-54.23 | 1.67-1.69 | w |

In one embodiment of the invention, the AlPO-57 is thermally stable up to a temperature of at least 400° C., and in another embodiment the AlPO-57 is thermally stable up to a temperature of at least 500° C.

When AlPO-57 is calcined in air and ambient water vapor, there can be loss of metal from the framework, such as Al, which can alter the x-ray diffraction pattern from that observed for the as-synthesized AlPO-57 (See Studies in Surface Science, (2004) vol. 154, p. 1324-1331). Some AlPO-57 compositions may not be stable to air calcination and subsequent exposure to water. Stability to air calcinations is favored by AlPO-57 compositions containing some Si. The stable air-calcined AlPO-57 materials, AlPO-57C, are characterized by the empirical formula:

$$H_a M^{2+}_m EP_x Si_y O_z$$

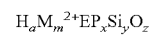

where M is at least one divalent metal cation selected from the group consisting of $Be^{2+}$, $Mg^{2+}$, $Zn^{2+}$, $Co^{2+}$, $Mn^{2+}$, $Fe^{2+}$, $Ni^{2+}$, "m" is the mole ratio of M to E and varies from 0 to about 1.0, H is a proton, "a" is the mole ratio of H to E and has a value of about 0.1 to about 2.0, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0.05 to about 1.0, "m"+"y"≥0.1, and "z" is the mole ratio of O to E and has a value determined by the equation:

$$z = (a + 2 \cdot m + 3 + 5 \cdot x + 4 \cdot y)/2$$

and is characterized in that it has the x-ray diffraction pattern having at least the d-spacings and intensities set forth in Table B:

TABLE B

| 2Θ | d (Å) | I/I₀ % |
|---|---|---|
| 8.03-7.52 | 11-11.75 | w-m |
| 10.65-10.28 | 8.3-8.6 | m-s |
| 13.61-13.2 | 6.5-6.7 | m-vs |
| 16.25-15.9 | 5.45-5.57 | w-m |
| 17.34-16.87 | 5.11-5.25 | w-s |
| 22.15-21.39 | 4.01-4.15 | s-vs |
| 22.9-22.32 | 3.88-3.98 | m-s |
| 23.64-23.14 | 3.76-3.84 | w-m |
| 26.67-26.03 | 3.34-3.42 | w-m |
| 27.33-26.83 | 3.26-3.32 | w-m |
| 30.06-29.46 | 2.97-3.03 | w-m |
| 32.53-31.82 | 2.75-2.81 | w-m |

The crystalline AlPO-57 materials of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The AlPO-57 compositions of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanol to olefins, methanation and syngas shift process. Specific reaction conditions and the types of feeds which can be used in these processes are set forth in U.S. Pat. No. 4,310,440, U.S. Pat. No. 4,440,871 and U.S. Pat. No. 5,126,308, which are incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of 400° to 1200° F. (204-649° C.), preferably between 600° and 950° F. (316-510° C.). Reaction pressures are in the range of atmospheric to about 3,500 psig (24,132 kPa g), preferably between 200 and 3000 psig (1379-20,685 kPa g). Contact times usually correspond to liquid hourly space velocities (LHSV) in the range of about 0.1 $hr^{-1}$ to 15 $hr^{-1}$, preferably between about 0.2 and 3 $hr^{-1}$. Hydrogen circulation rates are in the range of 1,000 to 50,000 standard cubic feet (scf) per barrel of charge (178-8,888 std. $m^3/m^3$), preferably between 2,000 and 30,000 scf per barrel of charge (355-5,333 std. $m^3/m^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the AlPO-57 composition using feedstocks such as gas oils, heavy naphthas, deasphalted crude oil residua, etc. with gasoline being the principal desired product. Temperature conditions of 850° to 1100° F., LHSV values of 0.5 to 10 and pressure conditions of from about 0 to 50 psig are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 5:1 and 30:1, a LHSV of about 0.3 to about 6 $hr^{-1}$, a temperature of about 100° to about 250° C. and pressures of about 200 to about 1000 psig. Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,894 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference.

The conversion of methanol to olefins is effected by contacting the methanol with the AlPO-57 catalyst at conversion conditions, thereby forming the desired olefins. The methanol can be in the liquid or vapor phase with the vapor phase being preferred. Contacting the methanol with the AlPO-57 catalyst can be done in a continuous mode or a batch mode with a continuous mode being preferred. The amount of time that the methanol is in contact with the AlPO-57 catalyst must be sufficient to convert the methanol to the desired light olefin products. When the process is carried out in a batch process, the contact time varies from about 0.001 hrs to about 1 hr and preferably from about 0.01 hr to about 1.0 hr. The longer contact times are used at lower temperatures while shorter times are used at higher temperatures. Further, when the process is carried out in a continuous mode, the Weight Hourly Space Velocity (WHSV) based on methanol can vary from about 1 $hr^{-1}$ to about 1000 $hr^{-1}$ and preferably from about 1 $hr^{-1}$ to about 100 $hr^{-1}$.

Generally, the process must be carried out at elevated temperatures in order to form light olefins at a fast enough rate. Thus, the process should be carried out at a temperature of about 300° C. to about 600° C., preferably from about 400° C. to about 550° C. and most preferably from about 450° C. to about 525° C. The process may be carried out over a wide range of pressure including autogenous pressure. Thus, the pressure can vary from about 0 kPa (0 psig) to about 1724 kPa (250 psig) and preferably from about 34 kPa (5 psig) to about 345 kPa (50 psig).

Optionally, the methanol feedstock may be diluted with an inert diluent in order to more efficiently convert the methanol to olefins. Examples of the diluents which may be used are helium, argon, nitrogen, carbon monoxide, carbon dioxide, hydrogen, steam, paraffinic hydrocarbons, e.g., methane, aromatic hydrocarbons, e.g., benzene, toluene and mixtures thereof. The amount of diluent used can vary considerably and is usually from about 5 to about 90 mole percent of the feedstock and preferably from about 25 to about 75 mole percent.

The actual configuration of the reaction zone may be any well known catalyst reaction apparatus known in the art. Thus, a single reaction zone or a number of zones arranged in series or parallel may be used. In such reaction zones the methanol feedstock is flowed through a bed containing the AlPO-57 catalyst. When multiple reaction zones are used, one or more AlPO-57 catalysts may be used in series to produce the desired product mixture. Instead of a fixed bed, a dynamic bed system, e.g., fluidized or moving, may be used. Such a dynamic system would facilitate any regeneration of the AlPO-57 catalyst that may be required. If regeneration is required, the AlPO-57 catalyst can be continuously introduced as a moving bed to a regeneration zone where it can be regenerated by means such as oxidation in an oxygen containing atmosphere to remove carbonaceous materials.

The following examples are presented in illustration of this invention and are not intended as undue limitations on the generally broad scope of the invention as set out in the appended claims. The products will be designated with names that contain the suffix "-59" to indicate the "-59" structure and prefix that reflects the compositional nature of the product, such as "SAPO" for a silicoaluminophosphate, ZAPO for a zinc aluminophosphate, and MAPSO for a magnesium silicoaluminophosphate, etc.

The structure of the AlPO-57 compositions of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of $100 \times I/I_o$, the above designations are defined as:

$w=0-15; m=15-60; s=60-80$ and $vs=80-100$

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Example 1

A Teflon beaker was charged with 97.76 g DEDMAOH (20%), which was then stirred with a high speed mixer. Added 2.00 g $Zn(OAc)_2 \cdot 2 H_2O$ solid to the mixture, which dissolved in a few minutes. Then 4.44 g $Al(OH)_3$ (80%) was added slowly to the stirring reaction mixture in 4 separate portions. After an hour, 12.11 g $H_3PO_4$ (85%) was added to the hazy reaction mixture. After stirring for an hour, the final reaction mixture was a solution. The reaction mixture was loaded into 7 teflon-lined autoclaves and digested at 95° C. for 157 hours and 125, 150, and 175° C. at autogenous pressure for 37 and 157 hrs. The solid products were isolated and washed with de-ionized water via centrifugation. The products isolated from the 125° C./157 hr reaction and the 150 and 175° C. reactions were identified as ZAPO-57 via powder x-ray diffraction. Table 1 below shows representative diffraction lines for the 175° C./37 hour product. Elemental analysis showed this product had the elemental ratios C/N=5.86, Al/P=0.72, Zn/P=0.28, N/P=0.26, consistent with a stoichiometry of $DEDMA_{0.36}Zn_{0.39}AlP_{1.38}O_{5.52}$.

TABLE 1

| 2-Θ | d (Å) | $I/I_0$ (%) |
|---|---|---|
| 7.62 | 11.59 | w |
| 10.28 | 8.60 | s |
| 13.22 | 6.69 | m |
| 15.27 | 5.80 | w |
| 15.80 | 5.61 | w |
| 16.76 | 5.29 | m |
| 19.13 | 4.64 | w |
| 20.25 | 4.38 | w |
| 20.66 | 4.30 | w |
| 21.40 | 4.15 | vs |
| 22.16 | 4.01 | m |
| 22.98 | 3.87 | m |
| 24.60 | 3.62 | w |
| 25.87 | 3.44 | w |
| 26.58 | 3.35 | m |
| 28.58 | 3.12 | w |
| 28.92 | 3.08 | m |
| 29.18 | 3.06 | m |
| 31.09 | 2.87 | w |
| 31.60 | 2.83 | m |
| 31.90 | 2.80 | w |
| 33.87 | 2.64 | w |
| 34.66 | 2.59 | w |
| 35.44 | 2.53 | w |
| 42.00 | 2.15 | w |
| 42.28 | 2.14 | w |
| 48.44 | 1.88 | w |
| 48.96 | 1.86 | w |
| 49.80 | 1.83 | w |
| 50.66 | 1.80 | w |
| 54.44 | 1.68 | w |
| 54.78 | 1.67 | w |

Example 2

A Teflon beaker was charged with 97.76 g DEDMAOH (20%), which was then stirred with a high speed mixer. Added 4.60 g $Al(OH)_3$ (26.7% Al) in 5 portions, allowing the reaction mixture to stir between additions. This resulted in a clear solution. Next, 12.11 g $H_3PO_4$ (85%) was diluted with 3.00 g de-ionized water and poured into the reaction mixture with vigorous stirring. The reaction mixture remained a clear solution. Separately, 1.95 g $Mg(OAc)_2 \cdot 4H_2O$ was dissolved in 10.00 g de-ionized water. This solution was added slowly in a dropwise fashion to the reaction mixture with vigorous mixing. After some post addition stirring, the reaction mixture is a solution. The reaction mixture was placed in a Teflon-lined autoclave and digested at 175° C. for 40 hours. The solid product was isolated and washed with de-ionized water via centrifugation. The product was identified as MAPO-57 by powder x-ray diffraction. Representative diffraction lines are given for the product in Table 2 below. Elemental analysis showed this product had the elemental ratios Al/P=0.74, Mg/P=0.26, N/P=0.26, consistent with a stoichiometry of $DEDMA_{0.35}Mg_{0.35}AlP_{1.35}O_{5.4}$.

TABLE 2

| 2-Θ | d (Å) | I/I₀ (%) |
|---|---|---|
| 7.59 | 11.63 | w |
| 10.24 | 8.63 | s |
| 13.16 | 6.72 | m |
| 15.22 | 5.82 | w |
| 15.75 | 5.62 | w |
| 16.70 | 5.30 | m |
| 19.10 | 4.64 | m |
| 20.16 | 4.40 | w |
| 20.56 | 4.32 | w |
| 20.71 | 4.29 | w |
| 21.32 | 4.16 | vs |
| 21.76 | 4.08 | w |
| 22.10 | 4.02 | s |
| 22.70 | 3.91 | w |
| 22.90 | 3.88 | m |
| 24.50 | 3.63 | w |
| 25.81 | 3.45 | w |
| 26.50 | 3.36 | m |
| 28.48 | 3.13 | w |
| 28.82 | 3.10 | m |
| 29.08 | 3.07 | m |
| 30.96 | 2.89 | w |
| 31.48 | 2.84 | m |
| 31.80 | 2.81 | w |
| 33.80 | 2.65 | w |
| 34.56 | 2.59 | m |
| 34.89 | 2.57 | w |
| 35.32 | 2.54 | w |
| 36.41 | 2.47 | w |
| 37.30 | 2.41 | w |
| 39.28 | 2.29 | w |
| 41.22 | 2.19 | w |
| 41.86 | 2.16 | w |
| 42.16 | 2.14 | w |
| 48.03 | 1.89 | w |
| 48.24 | 1.88 | w |
| 48.82 | 1.86 | w |
| 49.66 | 1.83 | w |
| 50.50 | 1.81 | w |
| 54.27 | 1.69 | w |
| 54.56 | 1.68 | w |

Example 3

A Teflon beaker was charged with 97.76 g DEDMAOH (20%), which was stirred with a high speed mixer. To this was added 4.44 g of Al(OH)₃ (80.0%) in several aliquots with stirring in between. After the addition was completed, further stirring of the reaction mixture yielded a solution. Separately, 15.76 g H₃PO₄ (85%) was diluted with 5.10 g deionized H₂O. This solution was added to the reaction mixture dropwise over a 5 minute period. The reaction mixture remained a clear solution. Separately, Mg(OAc)₂*4H₂O (1.95 g) was dissolved in 7.38 g de-ionized water. This solution was added dropwise to the reaction mixture, which was further homogenized after the addition. A clear solution resulted. The solution was distributed among 5 Teflon-lined autoclaves and digested at autogenous pressure. The portions of the reaction mixture digested at 150° C. and 175° C. for 46 hours formed MAPO-57, as determined by powder x-ray diffraction. Representative diffraction lines for the 150° C. product are given below in Table 3.

TABLE 3

| 2-Θ | d (Å) | I/I₀ (%) |
|---|---|---|
| 7.65 | 11.55 | w |
| 10.38 | 8.52 | m |
| 13.20 | 6.70 | m |

TABLE 3-continued

| 2-Θ | d (Å) | I/I₀ (%) |
|---|---|---|
| 15.23 | 5.81 | w |
| 16.82 | 5.27 | m |
| 18.96 | 4.68 | w |
| 20.22 | 4.39 | w |
| 20.48 | 4.33 | w |
| 21.44 | 4.14 | vs |
| 21.88 | 4.06 | m |
| 22.98 | 3.87 | m |
| 25.68 | 3.47 | w |
| 26.58 | 3.35 | m |
| 28.82 | 3.10 | m |
| 31.60 | 2.83 | m |
| 34.58 | 2.59 | w |
| 35.42 | 2.53 | w |
| 41.96 | 2.15 | w |
| 42.36 | 2.13 | w |
| 48.32 | 1.88 | w |
| 48.98 | 1.86 | w |
| 50.62 | 1.80 | w |
| 54.66 | 1.68 | w |

Example 4

A Teflon beaker was charged with 100.00 g DEDMAOH (20%), which was then stirred with a high speed mixer. To this was added 4.09 g Al(OH)₃ (80.0%) in several aliquots with stirring in between. When the Al(OH)₃ was nearly totally dissolved, 12.90 g H₃PO₄ (85%) was added dropwise, but rapidly. This resulted in a clear solution. Separately, 3.00 g Mg(OAc)₂*4H₂O was dissolved in 12.00 g deionized water. This solution was added dropwise to the reaction mixture. A very small amount of solid appeared during this addition, but it cleared up with stirring. The reaction mixture was distributed among 4 Teflon-lined autoclaves and digested at autogenous pressure at 150 and 175° C. Products were isolated by centrifugation and washed with de-ionized water. The products resulting from digestions at 150° C. for 44 and 163 hours and at 175° C. for 44 hours were identified as MAPO-57 by powder x-ray diffraction. Representative diffraction lines for MAPO-57 from the 150° C./44 hour product are given below in Table 4.

TABLE 4

| 2-Θ | d (Å) | I/I₀ (%) |
|---|---|---|
| 7.60 | 11.62 | w |
| 10.26 | 8.62 | m |
| 13.16 | 6.72 | w |
| 13.78 | 6.42 | w |
| 15.20 | 5.82 | w |
| 15.76 | 5.62 | w |
| 16.72 | 5.30 | m |
| 19.10 | 4.64 | w |
| 20.18 | 4.40 | w |
| 20.74 | 4.28 | m |
| 21.32 | 4.16 | s |
| 21.76 | 4.08 | w |
| 22.12 | 4.02 | vs |
| 22.90 | 3.88 | w |
| 24.50 | 3.63 | w |
| 25.82 | 3.45 | w |
| 26.50 | 3.36 | w |
| 27.76 | 3.21 | w |
| 28.48 | 3.13 | w |
| 28.84 | 3.09 | m |
| 29.08 | 3.07 | m |
| 30.98 | 2.88 | w |
| 31.50 | 2.84 | m |
| 31.82 | 2.81 | w |

TABLE 4-continued

| 2-Θ | d (Å) | I/I$_0$ (%) |
|---|---|---|
| 34.56 | 2.59 | w |
| 34.94 | 2.57 | w |
| 35.29 | 2.54 | w |
| 37.33 | 2.41 | w |
| 40.21 | 2.24 | w |
| 41.20 | 2.19 | w |
| 41.88 | 2.16 | w |
| 42.16 | 2.14 | w |
| 42.96 | 2.10 | w |
| 43.82 | 2.06 | w |
| 47.20 | 1.92 | w |
| 48.26 | 1.88 | w |
| 48.80 | 1.86 | w |
| 49.66 | 1.83 | w |
| 50.48 | 1.81 | w |
| 54.30 | 1.69 | w |
| 54.54 | 1.68 | w |

Example 5

A Teflon beaker was charged with 100.00 g DEDMAOH (20%), which was then stirred with a high speed mixer. To this was added 4.47 g Al(OH)$_3$ (78.1%), a little at a time with stirring in between. To the resulting slightly hazy reaction mixture, 12.89 g H$_3$PO$_4$ (85 wt. %) was added dropwise with continued stirring. Separately, a solution was prepared by dissolving 1.64 g Zn(OAc)$_2$*2H$_2$O and 0.93 g Co(OAc)$_2$*4H$_2$O together in 13.23 g de-ionized water. This solution was added dropwise to the reaction mixture, which was further homogenized. The final reaction mixture is a pink and clear solution that was distributed among 7 Teflon-lined autoclaves which were digested at various temperatures and times at autogenous pressure. Products were isolated by centrifugation and washed with de-ionized water. The portions of the reaction mixture digested at 150° C. for 57 and 154 hours yielded products identified as MAPO-57 as determined by powder x-ray diffraction. Representative diffraction lines for the MAPO-57 products are given in Table 5 below. These two products were combined and analyzed yielding the elemental ratios Al/P=0.76, Zn/P=0.23, Co/P=0.06, and N/P=0.25, which corresponds to a stoichiometry of DEDMA$_{0.33}$Co$_{0.08}$Zn$_{0.30}$AlP$_{1.32}$O$_{5.35}$.

TABLE 5

| 2-Θ | d (Å) | I/I$_0$ (%) |
|---|---|---|
| 7.54 | 11.72 | w |
| 10.26 | 8.62 | s |
| 13.18 | 6.71 | m |
| 15.24 | 5.81 | w |
| 15.76 | 5.62 | w |
| 16.72 | 5.30 | m |
| 19.14 | 4.63 | w |
| 20.20 | 4.39 | w |
| 20.68 | 4.29 | w |
| 21.38 | 4.15 | vs |
| 22.14 | 4.01 | m |
| 22.96 | 3.87 | m |
| 24.58 | 3.62 | w |
| 25.84 | 3.44 | w |
| 26.56 | 3.35 | m |
| 28.56 | 3.12 | w |
| 28.88 | 3.09 | m |
| 29.14 | 3.06 | m |
| 31.58 | 2.83 | m |
| 31.88 | 2.80 | w |
| 34.62 | 2.59 | w |
| 35.40 | 2.53 | w |
| 41.93 | 2.15 | w |
| 48.36 | 1.88 | w |
| 48.96 | 1.86 | w |
| 50.62 | 1.80 | w |
| 54.66 | 1.68 | w |

Example 6

A Teflon beaker was charged with 120.00 g DEDMAOH (20 wt. %), which was then stirred with a high speed mixer. Then Al(OH)$_3$ (78.1 wt. %), 5.58 g, was added in aliquots with stirring in between, yielding a clear solution. This was followed by the addition of 2.38 g TEOS (98 wt. %). The reaction mixture was allowed to stir for 1.5 hours to hydrolyze the TEOS. Next H$_3$PO$_4$ (85 wt. %), 15.47 g, was added dropwise over the next half hour. By the end of the addition, the reaction mixture was a solution. Separately, 2.40 g Mg(OAc)$_2$*4H$_2$O was dissolved in 10.00 g de-ionized water. This solution was added dropwise to the reaction mixture, which remained a solution throughout the addition. After stirring for another 30 minutes post-addition, 1.82 g HF (48 wt. %) was added dropwise to bring down the pH. The resulting clear solution was distributed among 7 Teflon-lined autoclaves and digested at a variety of temperatures and time periods. Products were isolated by centrifugation and washed with de-ionized water. The products from the 175° C. digestions (54 and 141 hours) yielded MAPSO-57 as determined by x-ray diffraction. Representative diffraction lines for the product are given below in Table 6. Elemental analysis yielded the elemental ratios P/Si=8, Al/(P+Si)=0.81, Mg/(P+Si)=0.32, and N/(P+Si)=0.24, which corresponds to a metals stoichiometry of DEDMA$_{0.30}$Mg$_{0.40}$AlP$_{0.91}$Si$_{0.14}$.

TABLE 6

| 2-Θ | d (Å) | I/I$_0$ (%) |
|---|---|---|
| 7.47 | 11.83 | w |
| 10.26 | 8.62 | m |
| 13.14 | 6.73 | w |
| 13.78 | 6.42 | w |
| 15.20 | 5.83 | w |
| 15.78 | 5.61 | w |
| 16.70 | 5.30 | m |
| 19.08 | 4.65 | w |
| 20.18 | 4.40 | w |
| 20.78 | 4.27 | m |
| 21.32 | 4.16 | m |
| 22.12 | 4.02 | vs |
| 22.88 | 3.88 | w |
| 24.54 | 3.62 | w |
| 25.81 | 3.45 | w |
| 26.48 | 3.36 | w |
| 28.50 | 3.13 | w |
| 28.88 | 3.09 | s |
| 31.50 | 2.84 | m |
| 31.86 | 2.81 | w |
| 34.60 | 2.59 | w |
| 35.00 | 2.56 | w |
| 35.32 | 2.54 | w |
| 41.88 | 2.16 | w |
| 42.24 | 2.14 | w |
| 42.98 | 2.10 | w |
| 48.32 | 1.88 | w |
| 48.82 | 1.86 | w |
| 49.74 | 1.83 | w |
| 50.54 | 1.80 | w |
| 54.40 | 1.69 | w |

Example 7

A Teflon beaker was charged with 446.94 g DEDMAOH (20 wt. %), which was then stirred with a high speed mixer. To this 19.98 g Al(OH)$_3$ (78.1 wt. %) was added intermittently in many aliquots with stirring in between. Most of the Al(OH)$_3$ dissolved, leaving a slightly hazy solution. This was followed by the fast dropwise addition of 57.66 g H$_3$PO$_4$ (85 wt. %) while stirring continued. The reaction mixture was allowed to stir post-addition, but remained slightly hazy. Separately, 10.73 g Mg(OAc)$_2$*4H$_2$O was dissolved in 44.69 g de-ionized water. This solution was added dropwise to the reaction mixture, pausing to stir after every dropper full. The reaction mixture was homogenized for an additional 1.5 hours after the addition was complete, yielding a slightly hazy solution. The reaction mixture was then distributed among 6 teflon-lined autoaclaves, which were all digested at 175° C. for 39 hours at autogenous pressure. Products were isolated by centrifugation and washed with de-ionized water. The products from all six autoclaves were combined. Powder x-ray diffraction showed the product to be MAPO-57. Representative diffraction lines for the combined product are given in Table 7 below. Elemental analysis showed the product to composed of the elemental ratios Al/P=0.73, Mg/P=0.26, and N/P=0.28, consistent with a stoichiometry of DEDMA$_{0.38}$Mg$_{0.36}$AlP$_{1.37}$O$_{5.48}$.

TABLE 7

| 2-Θ | d(Å) | I/I(%) |
|---|---|---|
| 7.60 | 11.62 | w |
| 10.26 | 8.61 | s |
| 13.18 | 6.71 | m |
| 13.78 | 6.42 | w |
| 15.23 | 5.81 | w |
| 15.76 | 5.62 | w |
| 16.72 | 5.30 | s |
| 19.12 | 4.64 | w |
| 20.18 | 4.40 | w |
| 20.74 | 4.28 | w |
| 21.34 | 4.16 | vs |
| 21.78 | 4.08 | w |
| 22.12 | 4.02 | m |
| 22.92 | 3.88 | m |
| 24.54 | 3.62 | w |
| 25.84 | 3.45 | w |
| 26.52 | 3.36 | m |
| 28.50 | 3.13 | w |
| 28.84 | 3.09 | m |
| 29.10 | 3.07 | m |
| 31.02 | 2.88 | w |
| 31.50 | 2.84 | m |
| 31.82 | 2.81 | w |
| 33.80 | 2.65 | w |
| 34.58 | 2.59 | w |
| 34.99 | 2.56 | w |
| 35.32 | 2.54 | w |
| 36.40 | 2.47 | w |
| 37.36 | 2.41 | w |
| 39.30 | 2.29 | w |
| 40.24 | 2.24 | w |
| 41.25 | 2.19 | w |
| 41.90 | 2.15 | w |
| 42.18 | 2.14 | w |
| 43.82 | 2.06 | w |
| 48.26 | 1.88 | w |
| 48.82 | 1.86 | w |
| 49.68 | 1.83 | w |
| 50.50 | 1.81 | w |
| 54.34 | 1.69 | w |
| 54.58 | 1.68 | w |

Example 8

A Teflon beaker was charged with 120.60 g DEDMAOH (20 wt. %), which was then stirred with a high speed mixer. To this 10.90 g Al(OH)$_3$ (26.7 wt. % Al) was added while stirring over a period of about 10 minutes. This was followed by the dropwise addition of 15.57 g H$_3$PO$_4$ (85 wt. %) while stirring, the addition lasting about 15 minutes. Separately, 5.92 g Zn(OAc)$_2$*2H$_2$O was dissolved in 32.01 g de-ionized water. This solution was added to the reaction mixture over a period of 30 minutes with continued stirring. The final reaction mixture was distributed among several Teflon-lined autoclaves, one of which was digested at 150° C. for 10 days. The product was isolated by centrifugation, washed with de-ionized water and dried at 100° C. overnight. Powder x-ray diffraction showed the product to be ZAPO-57. Representative diffraction lines for the product are given in Table 8 below.

TABLE 8

| 2-Θ | d(Å) | I/I$_0$(%) |
|---|---|---|
| 7.71 | 11.46 | w |
| 10.38 | 8.52 | s |
| 13.30 | 6.65 | m |
| 15.34 | 5.77 | w |
| 15.87 | 5.58 | w |
| 16.88 | 5.25 | m |
| 19.28 | 4.60 | w |
| 20.36 | 4.36 | w |
| 20.91 | 4.24 | w |
| 21.52 | 4.13 | vs |
| 22.31 | 3.98 | s |
| 23.08 | 3.85 | m |
| 24.72 | 3.60 | w |
| 26.01 | 3.42 | w |
| 26.72 | 3.33 | m |
| 28.70 | 3.11 | m |
| 29.02 | 3.07 | m |
| 29.28 | 3.05 | m |
| 31.20 | 2.86 | w |
| 31.72 | 2.82 | m |
| 32.04 | 2.79 | w |
| 34.78 | 2.58 | m |
| 35.52 | 2.53 | w |
| 42.14 | 2.14 | w |
| 42.46 | 2.13 | w |
| 44.62 | 2.03 | w |
| 48.56 | 1.87 | w |
| 49.10 | 1.85 | w |
| 49.96 | 1.82 | w |
| 50.80 | 1.80 | w |
| 54.60 | 1.68 | w |
| 54.87 | 1.67 | w |

Example 9

86.94 g DEDMAOH (20 wt. %) was placed in a Teflon bottle followed by the addition of 1.75 g Ludox AS-40 (40 wt. % SiO$_2$). The bottle was placed in an oven at 100° C. for 2 hours to dissolve the silica. The resulting solution was transferred to a Teflon beaker equipped with an overhead stirrer. Then 12.19 g Al(OH)$_3$ (26.7 wt. % Al) was added with stirring over a period of about 15 minutes. Next, 13.47 g H$_3$PO$_4$ (85%) was added to the reaction mixture, again with stirring. The reaction mixture was allowed to stir 40 minutes. Separately, 2.56 g Zn(OAc)$_2$*2H$_2$O was dissolved in 8.10 g de-ionized water. This solution was added to the reaction mixture over a period of 15 minutes. After stirring, the reaction mixture was distributed between two Teflon-lined 125 mL Parr autoclaves and digested at 150 and 175° C. for 90 hours. The products were isolated by centrifugation and were washed with de-ionized water. Both products formed ZAPSO-57 as identified by powder x-ray diffraction. The representative diffraction lines for the 175° C. product are shown in Table 9a. A portion of this material was calcined in air by ramping at 1° C./min to 500° C. and holding at that temperature for 4 hours. The diffraction pattern shows a slight shift from that observed for the as-synthesized material and was identified as ZAPSO-57C, the representative lines of which are listed in Table 9b. Elemental analysis on the calcined sample showed a metals stoichiometry of $Zn_{0.11}AlP_{0.59}Si_{0.11}$. The calcined sample had a BET surface area of 275 m²/g and a micropore volume of 0.12 g/cc.

TABLE 9a

ZAPSO-57

| 2-Θ | d(Å) | I/I₀(%) |
|---|---|---|
| 7.54 | 11.71 | w |
| 10.20 | 8.66 | s |
| 13.12 | 6.74 | m |
| 15.20 | 5.83 | w |
| 15.76 | 5.62 | w |
| 16.66 | 5.32 | m |
| 18.42 | 4.81 | w |
| 19.10 | 4.64 | w |
| 20.18 | 4.40 | w |
| 20.58 | 4.31 | w |
| 21.32 | 4.16 | vs |
| 22.16 | 4.01 | m |
| 22.88 | 3.88 | m |
| 24.56 | 3.62 | w |
| 25.84 | 3.45 | w |
| 26.50 | 3.36 | m |
| 28.48 | 3.13 | w |
| 28.92 | 3.08 | m |
| 29.12 | 3.06 | m |
| 31.00 | 2.88 | w |
| 31.50 | 2.84 | m |
| 31.88 | 2.80 | w |
| 34.66 | 2.59 | w |
| 35.28 | 2.54 | w |
| 41.96 | 2.15 | w |
| 42.30 | 2.14 | w |
| 48.30 | 1.88 | w |
| 48.86 | 1.86 | w |
| 50.60 | 1.80 | w |
| 54.54 | 1.68 | w |

TABLE 9b

ZAPSO-57C

| 2-Θ | d(Å) | I/I₀(%) |
|---|---|---|
| 7.76 | 11.39 | w |
| 10.46 | 8.45 | vs |
| 13.44 | 6.58 | s |
| 14.08 | 6.29 | w |
| 16.05 | 5.52 | w |
| 17.08 | 5.19 | m |
| 21.76 | 4.08 | s |
| 22.60 | 3.93 | m |
| 23.38 | 3.80 | m |
| 25.02 | 3.56 | w |
| 26.34 | 3.38 | m |
| 27.06 | 3.29 | m |
| 29.07 | 3.07 | w |
| 29.68 | 3.01 | m |
| 32.08 | 2.79 | m |
| 32.41 | 2.76 | w |

Example 10

To a Teflon bottle, 104.89 g DEDMAOH (20 wt. %) was added followed by the addition of 1.47 g Ludox AS-40 (40 wt. % SiO₂). The bottle was placed in a 100° C. oven for an hour to dissolved the silica. The resulting clear solution was transferred to a Teflon beaker with an overhead stirrer. Next, over a period of about 20 minutes, 5.11 g Al(OH)₃ (26.7 wt. % Al) was added to the reaction mixture while stirring. This was followed by the addition of 13.54 g H₃PO₄ (85 wt. %) while stirring over a period of 15 minutes. The resulting reaction mixture was a white opaque liquid which was distributed between two Teflon-lined autoclaves and digested at 150° C. and 175° C. After a 161 hour digestion, the products were isolated by centrifugation and washed with de-ionized water. The 175° C. product was identified as SAPO-57 by powder x-ray diffraction. Representative diffraction lines for the product are shown in Table 10 below.

TABLE 10

| 2-Θ | d(Å) | I/I₀(%) |
|---|---|---|
| 7.58 | 11.65 | w |
| 10.24 | 8.63 | s |
| 13.14 | 6.73 | m |
| 15.20 | 5.83 | w |
| 15.80 | 5.60 | w |
| 16.72 | 5.30 | m |
| 18.30* | 4.84* | w* |
| 19.14 | 4.63 | w |
| 20.16 | 4.40 | w |
| 20.50 | 4.33 | m |
| 21.34 | 4.16 | vs |
| 21.82 | 4.07 | m |
| 22.18 | 4.00 | m |
| 22.90 | 3.88 | m |
| 24.56 | 3.62 | w |
| 25.86 | 3.44 | w |
| 26.48 | 3.36 | m |
| 28.46 | 3.13 | w |
| 28.94 | 3.08 | m |
| 31.50 | 2.84 | m |
| 31.86 | 2.81 | w |
| 34.64 | 2.59 | w |
| 35.32 | 2.54 | w |
| 41.92 | 2.15 | w |
| 42.26 | 2.14 | w |
| 48.28 | 1.88 | w |
| 48.82 | 1.86 | w |
| 49.85 | 1.83 | w |
| 50.58 | 1.80 | w |
| 54.52 | 1.68 | w |

*MgO impurity from Al(OH)₃

What is claimed is:

1. A hydrocarbon conversion process comprising contacting a hydrocarbon stream with a catalyst at hydrocarbon conversion conditions to generate at least one converted product, wherein the catalyst is selected from the group consisting of a microporous crystalline AlPO-57 material, a microporous crystalline AlPO-57M material, a microporous crystalline AlPO-57C material, or mixtures thereof, where the microporous crystalline AlPO-57 material comprises a three-dimensional framework of $EO_2^-$, $PO_2^+$ and at least one of $[M^{2+}O_2]^{2-}$ and $SiO_2$ tetrahedral units and an empirical composition in the as synthesized and anhydrous basis expressed by an empirical formula of:

$$R_r M_m^{2+} E P_x Si_y O_z$$

where M is at least one divalent metal framework cation selected from the group consisting of alkaline earth and transition metals, "m" is the mole ratio of M to E and varies from 0 to about 1.0, R is an organoammonium cation selected from the group of ethyltrimethylammonium (ETMA$^+$), choline, diethyldimethylammonium (DEDMA$^+$), trimethylpropylammonium, tetramethylammonium (TMA$^+$), tetraethylammonium (TEA$^+$), tetrapropylammonium (TPA$^+$) and mixtures thereof, "r" is the mole ratio of R to E and has a value of about 0.1 to about 2.0, E is a trivalent element selected from the group consisting of aluminum, gallium, iron, boron and mixtures thereof, "x" is the mole ratio of P to E and varies from 0.5 to about 2.0, "y" is the mole ratio of Si to E and varies from 0 to about 1.0, "m"+"y"≥0.1, and "z" is the mole ratio of O to E and has a value determined by the equation:

$$z=(2\cdot m+r+3+5\cdot x+4\cdot y)/2$$

and is characterized in that it has the x-ray diffraction pattern having at least the d-spacings and intensities set forth in Table A:

TABLE A

| 2Θ | d(Å) | I/I$_0$ % |
|---|---|---|
| 7.85-7.36 | 11.25-12.00 | w |
| 10.49-10.11 | 8.43-8.74 | m-vs |
| 13.40-13.03 | 6.60-6.79 | w-m |
| 15.40-15.13 | 5.75-5.85 | w |
| 17.00-16.56 | 5.21-5.35 | m-s |
| 19.41-18.87 | 4.57-4.70 | w-m |
| 20.49-20.03 | 4.33-4.43 | w |
| 21.09-20.35 | 4.21-4.36 | w-m |
| 21.66-21.24 | 4.10-4.18 | m-vs |
| 22.43-21.98 | 3.96-4.04 | m-vs |
| 23.14-22.78 | 3.84-3.90 | w-m |
| 26.11-25.58 | 3.41-3.48 | w |
| 26.91-26.35 | 3.31-3.38 | w-m |
| 29.16-28.68 | 3.06-3.11 | m-s |
| 31.94-31.36 | 2.80-2.85 | m |
| 35.02-34.33 | 2.56-2.61 | w-m |
| 35.74-35.16 | 2.51-2.55 | w |
| 42.61-41.99 | 2.12-2.15 | w |
| 48.93-48.10 | 1.86-1.89 | w |
| 49.50-48.65 | 1.84-1.87 | w |
| 50.98-50.37 | 1.79-1.81 | w |
| 54.94-54.23 | 1.67-1.69 | w | the microporous crystalline AlPO-57M material comprises a three-dimensional framework of EO$_2^-$, PO$_2^+$ and at least one of [M$^{2+}$O$_2$]$^{2-}$ and SiO$_2$ tetrahedral units the composition given by the empirical formula:

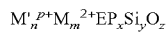

where M is at least one divalent framework metal cation selected from the group consisting of Be$^{2+}$, Mg$^{2+}$, Zn$^{2+}$, Co$^{2+}$, Mn$^{2+}$, Fe$^{2+}$, Ni$^{2+}$ and mixtures thereof, "m" is the mole ratio of M to E and varies from 0 to about 1.0, M' is NH$_4^+$, H$^+$, alkali metals, alkaline earth metals, and rare earth metals and mixtures thereof, "n" is the mole ratio of M' to E and has a value of about 0.03 to about 2.0, "p" is the weighted average valence of M', E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, "m"+"y"≥0.1, and "z" is the mole ratio of O to E and has a value determined by the equation:

$$z=(p\cdot n+2\cdot m+3+5\cdot x+4\cdot y)/2$$

and is characterized in that it has the x-ray diffraction pattern having at least the d-spacings and intensities set forth in Table A:

TABLE A

| 2Θ | d(Å) | I/I$_0$ % |
|---|---|---|
| 7.85-7.36 | 11.25-12.00 | w |
| 10.49-10.11 | 8.43-8.74 | m-vs |
| 13.40-13.03 | 6.60-6.79 | w-m |
| 15.40-15.13 | 5.75-5.85 | w |
| 17.00-16.56 | 5.21-5.35 | m-s |
| 19.41-18.87 | 4.57-4.70 | w-m |
| 20.49-20.03 | 4.33-4.43 | w |
| 21.09-20.35 | 4.21-4.36 | w-m |
| 21.66-21.24 | 4.10-4.18 | m-vs |
| 22.43-21.98 | 3.96-4.04 | m-vs |
| 23.14-22.78 | 3.84-3.90 | w-m |
| 26.11-25.58 | 3.41-3.48 | w |
| 26.91-26.35 | 3.31-3.38 | w-m |
| 29.16-28.68 | 3.06-3.11 | m-s |
| 31.94-31.36 | 2.80-2.85 | m |
| 35.02-34.33 | 2.56-2.61 | w-m |
| 35.74-35.16 | 2.51-2.55 | w |
| 42.61-41.99 | 2.12-2.15 | w |
| 48.93-48.10 | 1.86-1.89 | w |
| 49.50-48.65 | 1.84-1.87 | w |
| 50.98-50.37 | 1.79-1.81 | w |
| 54.94-54.23 | 1.68-1.69 | w | and the microporous crystalline AlPO-57C material comprises a three-dimensional framework of EO$_2^-$, PO$_2^+$ and at least one of [M$^{2+}$O$_2$]$^{2-}$ and SiO$_2$ tetrahedral units characterized by the empirical formula:

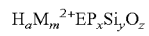

where M is at least one divalent framework metal cation selected from the group consisting of Be$^{2+}$, Mg$^{2+}$, Zn$^{2+}$, Co$^{2+}$, Mn$^{2+}$, Fe$^{2+}$, Ni$^{2+}$ and mixtures thereof, "m" is the mole ratio of M to E and varies from 0 to about 1.0, H is a proton, "a" is the mole ratio of H to E and has a value of about 0.1 to about 2.0, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0.05 to about 1.0, "m"+"y"≥0.1, and "z" is the mole ratio of O to E and has a value determined by the equation:

$$z=(a+2\cdot m+3+5\cdot x+4\cdot y)/2$$

and is characterized in that it has the x-ray diffraction pattern having at least the d-spacings and intensities set forth in Table B:

TABLE B

| 2Θ | d(Å) | I/I$_0$ % |
|---|---|---|
| 8.03-7.52 | 11-11.75 | w-m |
| 10.65-10.28 | 8.3-8.6 | m-s |
| 13.61-13.2 | 6.5-6.7 | m-vs |
| 16.25-15.9 | 5.45-5.57 | w-m |
| 17.34-16.87 | 5.11-5.25 | w-s |
| 22.15-21.39 | 4.01-4.15 | s-vs |
| 22.9-22.32 | 3.88-3.98 | m-s |
| 23.64-23.14 | 3.76-3.84 | w-m |
| 26.67-26.03 | 3.34-3.42 | w-m |
| 27.33-26.83 | 3.26-3.32 | w-m |
| 30.06-29.46 | 2.97-3.03 | w-m |
| 32.53-31.82 | 2.75-2.81 | w-m. |

2. The process of claim 1 wherein the hydrocarbon conversion process is selected from the group consisting of cracking, hydrocracking, alkylation, isomerization, polymerization, reforming, hydrogenation, dehydrogenation, transalkylation, dealkylation, hydration, dehydration, hydrotreating, hydrofining, hydrodenitrogenation, hydrodesulfurization, methanol to olefins, methanation, syngas shift process, olefin dimerization, oligomerization, dewaxing, and combinations thereof.

3. The process of claim 1 wherein the hydrocarbon conversion process is hydrocracking or hydrotreating wherein the hydrocracking or hydrotreating is operated at a temperature in the range of about 400° to about 1200° F. (204-649° C.) and a pressure in the range of atmospheric to about 3,500 psig (24,132 kPa g).

4. The process of claim 3 wherein the hydrocracking or hydrotreating is operated at liquid hourly space velocities (LHSV) in the range of about 0.1 hr$^{-1}$ to 15 hr$^{-1}$.

5. The process of claim 3 wherein the hydrocracking or hydrotreating is operated at hydrogen circulation rates in the range of 1,000 to 50,000 standard cubic feet (scf) per barrel of charge (178-8,888 std. m$^3$/m$^3$).

6. The process of claim 1 further comprising removing an effluent comprising the at least one converted product, fractionating the effluent, and recovering at least one converted product.

7. The process of claim 6 further comprising subjecting the effluent to partial condensation and vapor-liquid separation prior to fractionation.

8. The process of claim 6 further comprising recycling at least a portion of the effluent to the catalyst.

9. The process of claim 1 wherein the hydrocarbon conversion process comprises two stage operation and the catalyst is present in at least one of the two stages.

10. The process of claim 1 wherein the hydrocarbon conversion process is catalytic cracking operated at a temperature in the range of about 850° to about 1100° F., LHSV values of 0.5 to 10 and a pressure in the range of from about 0 to about 50 psig.

11. The process of claim 10 wherein the hydrocarbon stream is selected from the group consisting of gas oils, heavy naphthas, and deasphalted crude oil residua.

12. The process of claim 1 wherein the hydrocarbon conversion process is alkylation of aromatics and the converted product is at least one linear alkyl substituted aromatic, and wherein the process is operated at an aromatic:olefin mole ratio of between 5:1 and 30:1, a LHSV of about 0.3 to about 6 hr$^{-1}$, a temperature of about 100° to about 250° C. and a pressure of about 200 to about 1000 psig.

13. The process of claim 1 wherein the hydrocarbon conversion process is alkylation of isoparaffins with olefins and the converted product is at least one alkylate suitable as a motor fuel component, and wherein the process is operated at a temperature of from about −30° to 40° C., a pressure from about atmospheric to about 6,894 kPa (1,000 psig) and a weight hourly space velocity (WHSV) of 0.1 to about 120.

14. The process of claim 1 wherein the hydrocarbon conversion process is the conversion of methanol to olefins wherein the process is operated at a temperature of about 300° C. to about 600° C. and a pressure from about 0 kPa (0 psig) to about 1724 kPa (250 psig).

15. The process of claim 14 wherein the methanol is in the liquid or vapor phase and the operation is in a continuous or batch mode.

16. The process of claim 14 wherein the methanol is diluted with a diluent selected from the group consisting of helium, argon, nitrogen, carbon monoxide, carbon dioxide, hydrogen, steam, at least one paraffinic hydrocarbon, at least one aromatic hydrocarbon, and mixtures thereof.

17. The process of claim 1 wherein the catalyst is located in one or more catalyst zones arranged in series or parallel configuration, and wherein the catalyst may be in fixed beds or fluidized beds.

18. The process of claim 1 further comprising regenerating the catalyst.

19. A separation process comprising contacting at least two components with a material to generate at least one separated component, wherein the material is selected from the group consisting of a microporous crystalline AlPO-57 material, a microporous crystalline AlPO-57M material, a microporous crystalline AlPO-57C material, or mixtures thereof, where the microporous crystalline AlPO-57 material comprises a three-dimensional framework of EO$_2^-$, PO$_2^+$ and at least one of [M$^{2+}$O$_2$]$^{2-}$ and SiO$_2$ tetrahedral units and an empirical composition in the as synthesized and anhydrous basis expressed by an empirical formula of:

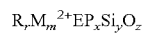

where M is at least one divalent metal framework cation selected from the group consisting of alkaline earth and transition metals, "m" is the mole ratio of M to E and varies from 0 to about 1.0, R is an organoammonium cation selected from the group of ethyltrimethylammonium (ETMA$^+$), choline, diethyldimethylammonium (DEDMA$^+$), trimethylpropylammonium, tetramethylammonium (TMA$^+$), tetraethylammonium (TEA$^+$), tetrapropylammonium (TPA$^+$) and mixtures thereof, "r" is the mole ratio of R to E and has a value of about 0.03 to about 2.0, E is a trivalent element selected from the group consisting of aluminum, gallium, iron, boron and mixtures thereof, "x" is the mole ratio of P to E and varies from 0.5 to about 2.0, "y" is the mole ratio of Si to E and varies from 0 to about 1.0, "m"+"y"≥0.1, and "z" is the mole ratio of O to E and has a value determined by the equation:

$$z=(2 \cdot m+r+3+5 \cdot x+4 \cdot y)/2$$

and is characterized in that it has the x-ray diffraction pattern having at least the d-spacings and intensities set forth in Table A:

TABLE A

| 2Θ | d(Å) | I/I$_0$ % |
|---|---|---|
| 7.85-7.36 | 11.25-12.00 | w |
| 10.49-10.11 | 8.43-8.74 | m-vs |
| 13.40-13.03 | 6.60-6.79 | w-m |
| 15.40-15.13 | 5.75-5.85 | w |
| 17.00-16.56 | 5.21-5.35 | m-s |
| 19.41-18.87 | 4.57-4.70 | w-m |
| 20.49-20.03 | 4.33-4.43 | w |
| 21.09-20.35 | 4.21-4.36 | w-m |
| 21.66-21.24 | 4.10-4.18 | m-vs |
| 22.43-21.98 | 3.96-4.04 | m-vs |
| 23.14-22.78 | 3.84-3.90 | w-m |
| 26.11-25.58 | 3.41-3.48 | w |
| 26.91-26.35 | 3.31-3.38 | w-m |
| 29.16-28.68 | 3.06-3.11 | m-s |
| 31.94-31.36 | 2.80-2.85 | m |
| 35.02-34.33 | 2.56-2.61 | w-m |
| 35.74-35.16 | 2.51-2.55 | w |
| 42.61-41.99 | 2.12-2.15 | w |
| 48.93-48.10 | 1.86-1.89 | w |
| 49.50-48.65 | 1.84-1.87 | w |
| 50.98-50.37 | 1.79-1.81 | w |
| 54.94-54.23 | 1.69-1.69 | w | the microporous crystalline AlPO-57M material comprises a three-dimensional framework of EO$_2^-$, PO$_2^+$ and at least one of [M$^{2+}$O$_2$]$^{2-}$ and SiO$_2$ tetrahedral units the composition given by the empirical formula:

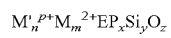

where M is at least one divalent framework metal cation selected from the group consisting of $Be^{2+}$, $Mg^{2+}$, $Zn^{2+}$, $Co^{2+}$, $Mn^{2+}$, $Fe^{2+}$, $Ni^{2+}$ and mixtures thereof, "m" is the mole ratio of M to E and varies from 0 to about 1.0, M' is $NH_4^+$, $H^+$, alkali metals, alkaline earth metals, and rare earth metals and mixtures thereof, "n" is the mole ratio of M' to E and has a value of about 0.03 to about 2.0, "p" is the weighted average valence of M', E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0 to about 1.0, "m"+"y"≥0.1, and "z" is the mole ratio of O to E and has a value determined by the equation:

$$z=(p \cdot n+2 \cdot m+3+5 \cdot x+4 \cdot y)/2$$

and is characterized in that it has the x-ray diffraction pattern having at least the d-spacings and intensities set forth in Table A:

TABLE A

| 2Θ | d(Å) | I/I$_0$ % |
|---|---|---|
| 7.85-7.36 | 11.25-12.00 | w |
| 10.49-10.11 | 8.43-8.74 | m-vs |
| 13.40-13.03 | 6.60-6.79 | w-m |
| 15.40-15.13 | 5.75-5.85 | w |
| 17.00-16.56 | 5.21-5.35 | m-s |
| 19.41-18.87 | 4.57-4.70 | w-m |
| 20.49-20.03 | 4.33-4.43 | w |
| 21.09-20.35 | 4.21-4.36 | w-m |
| 21.66-21.24 | 4.10-4.18 | m-vs |
| 22.43-21.98 | 3.96-4.04 | m-vs |
| 23.14-22.78 | 3.84-3.90 | w-m |
| 26.11-25.58 | 3.41-3.48 | w |
| 26.91-26.35 | 3.31-3.38 | w-m |
| 29.16-28.68 | 3.06-3.11 | m-s |
| 31.94-31.36 | 2.80-2.85 | m |
| 35.02-34.33 | 2.56-2.61 | w-m |
| 35.74-35.16 | 2.51-2.55 | w |
| 42.61-41.99 | 2.12-2.15 | w |
| 48.93-48.10 | 1.86-1.89 | w |
| 49.50-48.65 | 1.84-1.87 | w |
| 50.98-50.37 | 1.79-1.81 | w |
| 54.94-54.23 | 1.70-1.69 | w | and the microporous crystalline AlPO-57C material comprises a three-dimensional framework of $EO_2^-$, $PO_2^+$ and at least one of $[M^{2+}O_2]^{2-}$ and $SiO_2$ tetrahedral units characterized by the empirical formula:

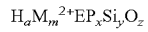

where M is at least one divalent framework metal cation selected from the group consisting of $Be^{2+}$, $Mg^{2+}$, $Zn^{2+}$, $Co^{2+}$, $Mn^{2+}$, $Fe^{2+}$, $Ni^{2+}$ and mixtures thereof, "m" is the mole ratio of M to E and varies from 0 to about 1.0, H is a proton, "a" is the mole ratio of H to E and has a value of about 0.1 to about 2.0, E is a trivalent element selected from the group consisting of aluminum, gallium, iron, boron and mixtures thereof, "x" is mole ratio of P to E and varies from 0.5 to about 2.0, "y" is the mole ratio of Si to E and varies from 0.05 to about 1.0, "m"+"y"≥0.1, and "z" is the mole ratio of O to E and has a value determined by the equation:

$$z=(a+2 \cdot m+3+5 \cdot x+4 \cdot y)/2$$

and is characterized in that it has the x-ray diffraction pattern having at least the d-spacings and intensities set forth in Table B:

TABLE B

| 2Θ | d(Å) | I/I$_0$ % |
|---|---|---|
| 8.03-7.52 | 11-11.75 | w-m |
| 10.65-10.28 | 8.3-8.6 | m-s |
| 13.61-13.2 | 6.5-6.7 | m-vs |
| 16.25-15.9 | 5.45-5.57 | w-m |
| 17.34-16.87 | 5.11-5.25 | w-s |
| 22.15-21.39 | 4.01-4.15 | s-vs |
| 22.9-22.32 | 3.88-3.98 | m-s |
| 23.64-23.14 | 3.76-3.84 | w-m |
| 26.67-26.03 | 3.34-3.42 | w-m |
| 27.33-26.83 | 3.26-3.32 | w-m |
| 30.06-29.46 | 2.97-3.03 | w-m |
| 32.53-31.82 | 2.75-2.81 | w-m. |

20. The process of claim 19 wherein the separation is based on molecular size of the components, degree of polarity of the components, or ion exchange of the components with the material.

* * * * *